United States Patent [19]

Wood

[11] 4,124,626

[45] Nov. 7, 1978

[54] CONTROL OF SWINE DYSENTERY WITH AV290 AND SALTS OR COMPLEXES THEREOF

[75] Inventor: Irwin B. Wood, Pennington, N.J.

[73] Assignee: American Cyanamid Co., Stamford, Conn.

[21] Appl. No.: 845,755

[22] Filed: Oct. 26, 1977

Related U.S. Application Data

[63] Continuation of Ser. No. 745,724, Nov. 29, 1976, abandoned.

[51] Int. Cl.$^2$ ............................................. A61K 35/00
[52] U.S. Cl. ................................................... 424/118
[58] Field of Search .......................................... 424/118

[56] References Cited

U.S. PATENT DOCUMENTS 3,338,786   8/1967   Kunstmann et al. ................ 424/118

*Primary Examiner*—Sam Rosen
*Attorney, Agent, or Firm*—H. G. Jackson

[57] ABSTRACT

This disclosure describes compositions of matter useful for the treatment and prophylaxis of hemorrhagic colitis in swine and the methods of controlling and preventing hemorrhagic colitis in swine therewith, the active ingredients of said compositions of matter being antibiotic AV290, antibiotic AV290 sulfate, an antibiotic AV290-syntan complex, an antibiotic AV290-alkyl sulfate complex, and/or an antibiotic AV290 alkylated derivative.

5 Claims, No Drawings

CONTROL OF SWINE DYSENTERY WITH AV290 AND SALTS OR COMPLEXES THEREOF

This application is a continuation of co-pending application Ser. No. 745,724 filed Nov. 29, 1976 which is now abandoned.

BRIEF SUMMARY OF THE INVENTION

This invention relates to novel compositions of matter useful in the veterinary field for the treatment and prophylaxis of hemorrhagic colitis in swine. More particularly, it relates to therapeutic and prophylatic compositions containing one or more of the following active ingredients (in any proportions) which are useful for the treatment and prevention of hemmorrhagic colitis in swine:

(1) antibiotic AV290 whose preparation and properties are disclosed in U.S. Pat. No. 3,338,786;

(2) antibiotic AV290 sulfate which is disclosed in U.S. Pat. No. 3,855,410;

(3) an antibiotic AV290-syntan complex prepared as described in U.S. Pat. No. 3,832,462;

(4) an antibiotic AV290-alkyl sulfate complex derived by treatment of the antibiotic with an alkali metal alkyl sulfate as set forth in U.S. Pat. No. 3,856,937;

(5) an antibiotic AV290 alkylated derivative derived by treatment of the antibiotic with a lower alkyl halide as defined and described in U.S. Pat. No. 3,954,973.

The invention includes not only the new compositions of matter but also the methods of controlling and preventing hemorrhagic colitis in swine. My invention is based upon the discovery that although the above-described active ingredients have been utilized for promoting the growth rate of poultry and farm animals, administration thereof has heretofore been at levels well below those required for the effective treatment and prevention of hemorrhagic colitis in swine. The above-cited U.S. Pat. Nos. 3,338,786; 3,832,462; 3,855,410; 3,856,937; and 3,954,973 are hereby incorporated by reference.

DETAILED DESCRIPTION OF THE INVENTION

Swine dysentery (bloody scours, hemorrhagic colitis) is one of the most destructive diseases encountered in swine husbandry. It is widespread disease affecting all continents, and when observed in pigs it is generally characterized by one or more of the following signs: diarrhea, stunted growth, staggering gait, swelling of the eyelids, and coarseness of the hair. Although the severity of the disease varies from animal to animal, it nevertheless must be considered as one of the most important economic and clinical problems encountered in the rearing of swine. This is evidenced by the fact that dysentery infections in pigs generally result in 25% mortality of the herd, and frequently produce 100% mortality. Moreover, diseased animals show a rapid loss of weight, and those cleared of the disease are subject to relapse and generally have a low market value.

In an attempt to overcome these difficulties and reduce losses due to the disease, a major effort has been made by researchers throughout the world to determine the origin of the disease in swine herds, and to provide an effective cure for the animals. While these efforts have met with some success, there still remains much to be done in each of these areas. For example, the origin of swine dysentery has not yet been clearly determined, although several organisms, such as Treponema, Vibrio, and Salmonella, have been found to be associated with outbreaks of the disease. Likewise, a plethora of prophylactic and therapeutic agents have been found to be partially effective in reducing dysentery infections and/or curing infected animals. However, none of the treatments heretofore utilized have been entirely satisfactory, even though such treatments have included a wide variety of drugs. Among the drugs utilized are the sulfa drugs, tetracycline-type antibiotics, mycin drugs, concentrated salines and alkalines, and arsenicals.

In accordance with this invention, I have found that the above-described active ingredients (either singly or in any combination) effect a complete cure of hemorrhagic colitis in swine when administered orally to infected swine in amounts ranging from about 5 mg. to about 50 mg. per kilogram of body weight per day for a period of from about 14 to about 21 days. A preferred dosage regimen for optimum results would be from about 10 mg. to about 25 mg. orally per kg. of body weight per day for a period of 14–21 days. Such dosage units are employed that a total of from about 80 mg. (for a 16 kg. piglet at 5 mg./kg.) to about 5 grams (for a 100 kg. hog or sow at 50 mg./kg.) of active ingredient are administered orally in a 24-hour period. The daily dosage may be administered as a single oral dose or as divided doses depending upon the exigencies of the therapeutic situation.

The dosage units of active ingredients may contain other inert or medically active materials, for instance, when the dosage unit form is a tablet, pill or granules, there may also be present various binders, fillers or solid diluents. Suitable materials for this purpose may be, for example, starch, such as corn starch, or sugar such as lactose or sucrose. When the dosage unit form is a capsule, it may contain in addition to materials of the above type of a liquid carrier such as a fatty oil. The dosage unit form may also have present excipients such as dicalcium phosphate. Various other materials may be present as coatings or to otherwise modify the physical form of the dosage unit, for instance, pills or capsules may be coated with shellac, sugar or both. Of course, any material used in preparing the dosage unit form should be pharmaceutically pure and substantially non-toxic in the amounts employed.

Where the drug is to be administered as a single oral dose, for example in a therapeutic treatment, 5.25% by weight of the drug may be mixed with 4.25% by weight of hydroxystearin and 90.50% by weight of sesame oil. This formulation is administered by a syringe as an oral paste and will provide about 250 mg. of drug per cubic centimeters(cc). It is, of course, obvious that a higher concentration of the drug can be achieved by altering the quantities of drug and sesame oil accordingly.

For prophylactic administration, the active ingredient is preferably administered either in the feed or in the drinking water at levels of from about 100 to about 1000 parts per million, and preferably at levels of from 200 to 500 parts per million. This treatment is usually effective when administered over about a one to three week period, although the treatment period may be extended if so desired. For prophylactic or therapeutic treatment of swine via feed treatment, any conventional swine feed may be employed, and a typical feed is described in Example 1 below.

As indicated above, the active ingredient is normally administered to the swine intimately mixed in the feed ration or drinking water for prophylaxis. The drug can be suitably prepared as a premix or feed supplement containing from about 1% to about 90% by weight of the formulation which can also contain various diluents or carriers. Carriers suitable for use to make up the feed supplement compositions include the following: soybean meal, alfalfa meal, cotton seed oil meal, cornmeal, cane molasses, urea, bone meal, corncob meal, dried fermentation whole harvest mash solids, and the like. The carrier promotes a uniform distribution of the drug in the finished feed with which the supplement is blended. It thus performs an important function by ensuring proper distribution of the drug throughout the feed. The feed supplement of premix containing the active ingredient can be readily mixed with the swine feed ration by any conventional technique for mixing feeds. For convenience in commercial use, it has been found that premixes containing from about 5% to about 15% by weight of the active ingredient are preferred. When administering the compound in drinking water, it has been found convenient to utilize water soluble excipients, e.g., lactose, dextrose, tartaric acid. The powder can be added to drinking water to provide an effective concentration level of active compound of from about 0.0025% to about 0.05% by weight.

Also in accordance with this invention, we have found that the above-identified swine dysentery control agents can be used in combination with other drugs such as antibacterial agents, antifungal agents, growth promoting agents, and the like, normally used in the raising of swine. In particular, we have found it advantageous to include in the diet of swine receiving the active ingredients, one or more of the following drugs administered in the prescribed concentration:

(a) from 5 to 150 ppm of a bis-(5-nitrofurfurylidene)-acetoneguanylhydrazone;

(b) from 10 to 300 ppm of a tetracycline antibiotic such as chlortetracycline, oxytetracycline, tetracycline or demethylchlortetracycline;

(c) from 10 to 300 ppm of a sulfa drug such as sulfadimethoxypyrimidine or sulfaethoxypyridazine; and (d) from 500 to 20,000 ppm of an alkali metal formaldehyde sulfoxylate or bisulfite, such as sodium formaldehyde bisulfite or sodium formaldehyde sulfoxylate.

A preferred combination of drugs to be used with either the prophylactic or the therapeutic swine dysentery treatment of this invention is the administration of 20 ppm of bis-(5-nitrofurfurylidene)acetoneguanylhydrazone with or without 100 ppm of chlortetracycline administered in the feed.

For a clearer understanding of the invention, specific examples of it are set forth below. These examples are merely illustrative, and are not to be understood as limiting the scope and underlying principles of the invention in any way.

EXAMPLE 1

Evaluation of the Efficacy of Antibiotic AV290 Sulfate for the Control of Hemorrhagic Colitis in Swine Test Material Antibiotic AV290 sulfate; 93.4% by weight of active ingredient.

PC-2 Swine grower mash (composition is given in Table I below).

Procedure

Thirty Hampshire X Yorkshire crossbred pigs (14 females, 16 castrated males) at 9 to 10 weeks of age were obtained for the test. Nine days before infection the pigs were weighed and ear-tagged. Two days later the animals were randomly alloted by weight, sex and litter to 6 pens of 5 pigs each (two pens per test) according to the following design:

| Group | No. of Pigs | Infection | Feed Medication (grams/ton) |
|---|---|---|---|
| A | 10 | No | None |
| B | 10 | Yes | None |
| C | 10 | Yes | AV290 Sulfate 200 g./ton a.i. |

Normal feed and water were provided ad libitum to all pigs. The pigs were weighed the day before infection (Average weight: 57 lbs./pig) and their feed removed at 4:00 pm. Twenty-two hours later the pigs were given non-medicated feed mixed with either phosphate buffered saline (PBS), 0.1M, pH 7.0, or PBS plus scrapings and contents from the colons of dysenteric pigs wherein the preparation of the inoculum is based on the procedure of D. L. Harris et al. *Can. J. Comp. Med.* 36: 74–76 (1972). Each pig to be infected is given 50 ml. of the inoculum mixed with 200 ml. of PBS and 227 grams of PC-2 ration. The pigs consume the infective material within 1 hour; the designed feed is provided at the time and continued for 28 days. Non-medicated feed is given to all pigs from days 29 to 42 when the experiment is terminated.

Records/pig
Feed consumption, daily
Body weight, weekly
Appearance of signs of swine dysentery disease, daily
Mortality, daily Results Severe, mucohemorrhagic diarrhea first occured in the infected, non-medicated pigs (Group B) on the fifth day post-infection. The incidence of severe scouring increased during the second and third weeks post-infection and reached its peak (100%) during the fourth and fifth weeks after infection. During the last week of the experiment, only about half of the surviving pigs had moderate to severe scouring.

Four of the infected, non-medicated pigs died during the experiment. *Treponema hyodisenteriae* was observed in the colonic contents of all four pigs at necropsy. Small spirochetes and vibrio-like organism were observed occasionally. Hemorrhagic necrosis of the colonic mucosa and hemorrhage or hemorrhagic necrosis of the stomach were found in all four dead pigs. The small intestines usually had thin walls and contained gas.

Two pigs in Group C (infected, medicated with 200 grams of antibiotic AV290 sulfate/ton of feed) developed moderate to sever mucohemorrhagic diarrhea on the fourteenth day post-infection. They continue to scour the third and fourth week after infection. During the last week of the experiment, however, all Group C pigs had relatively normal stools.

The results are summarized in Table II below.

Table I

| Composition of PC-2 Ration | |
|---|---|
| Ingredients | Percent in Ration |
| Ground yellow corn | 76.85 |
| Soybean oil meal, 44% protein | 16.25 |
| Meat and bone scraps, 50% protein | 2.50 |
| Dried whey | 2.50 |
| Dicalcium phosphate | 1.00 |
| Iodized salt | 0.50 |
| Ground limestone | 0.20 |
| Vitamin-trace mineral mix* | 0.20 |

Table I-continued

*Furnished the following ingredients per ton of diet.

| | |
|---|---|
| Vitamin A | 4,000,000 IU |
| Vitamin $D_2$ | 800,000 IU |
| Riboflavin | 8 g. |
| Pantothenic acid | 20 g. |
| Niacin | 40 g. |
| Vitamin $B_{12}$ | 20 mg. |
| Menadione (Source of Vitamin K) | 4 g. |
| Iron | 100 ppm |
| Copper | 10 ppm |
| Manganese | 60 ppm |
| Zinc | 100 ppm |

-continued

| Group | No. of Pigs | Infection | Feed Medication (grams/ton) |
|---|---|---|---|
| | | | 500 g./ton a.i. |

Experimental infections and conduct of the trial were similar to the procedures outlined in Example 1.

Results

Half of the infected, non-medicated pigs (Group B) developed moderate to severe mucohemorrhagic diahrrea on the third day post-infection. Scouring intensity

Table II

Evaluation of the Efficacy of Antibiotic AV290 Sulfate for the Control of Hermorrhagic Colitis in Swine

| Group | Survivors/ Totals | 6 Weeks Averages of Daily | | Average Body Weight kg./pig | | Average Daily Dosage of AV290 mg./kg of Body Weight (28 days data) |
|---|---|---|---|---|---|---|
| | | Feed Consumption kg./pig | Weight Gain kg./pig | Start | At 6 Wks. | |
| A Non-infected, Non-medicated | 10/10 | 1.93 | 0.64 | 26.13 | 53.25 | — |
| B Infected, Non-medicated | 6/10 | 0.83 | −0.03 | 26.04 | 27.71 | — |
| C Infected, Medicated with AV290 (220 g./ton feed) | 10/10 | 1.73 | 0.63 | 25.49 | 51.71 | 11.02 |

Similar results are obtained by substituting antibiotic AV290, an antibiotic AV290-syntan complex, an antibiotic AV290-alkyl sulfate complex, or an antibiotic AV290 alkylated derivative for antibiotic AV290 sulfate in the above experiment.

EXAMPLE 2

Evaluation of the Efficacy of Antibiotic AV290-Tru-Tan RT Regular ® Complex for the Control of Hemorrhagic Colitis in Swine Test Material Antibiotic AV290-Tru-Tan RT Regular ®; 2.7% by weight of active ingredient.

PC-2 Swine grower mash (composition is given in Table I of Example 1.

Procedure

Forty Hampshire X Yorkshire crossbred pigs (18 females, 22 castrated males) at 6 to 7 weeks of age were obtained for the test. Eight days before infection the pigs were weighed and ear-tagged. Three days later they were randomly alloted by weight, sex and litter to eight pens of five pigs each (two pens per tests) according to the following design:

| Group | No. of Pigs | Infection | Feed Medication (grams/ton) |
|---|---|---|---|
| A | 10 | No | None |
| B | 10 | Yes | None |
| C | 10 | Yes | AV290 Tru-tan 50 g./ton a.i. |
| D | 10 | Yes | AV290 Tru-tan | and incidence increased rapidly and all the Group B pigs scoured severly from day 10 through day 19 when the last pig died.

*Trepanoma hyodysenteriae* was observed in the colonic contents of all 10 pigs at necropsy. Vibrio-like organisms were seen in nine of the Group B pigs but small spirochetes were observed in only four pigs. Hyperemia, hemorrhage, necrosis or combinations thereof were seen in the stomachs and colons of all Group B pigs examined. No lesions were found in the small intestines. This pathological picture is typical of swine dysentery.

In the Group C pigs receiving only 50 ppm of the AV290 complex in the feed, mortality occurred between days 6 and 21 and reached 80%. *Trepanoma hyodysenteriae* and vibrio-like organisms were observed in the colonic contents of all eight pigs at necropsy; no small spirochetes were seen. Hyperemia, hemorrhage, necrosis or combinations thereof were seen in all stomachs and colons but no lesions were found in the small intestines.

One of the pigs in Group D receiving 500 ppm of the AV290 complex in the feed developed moderate mucohemorrhagic diarrhea on day 3. The pig continued to scour moderately until it died on day 8. On the same day two pigs also began to scour moderately to severely. One of these pigs died on day 11, and the other died on day 25, following irregular periods of moderate to sever diarrhea. Two pigs in Group D developed moderate to severe diarrhea during the last 3 days of the experiment. The surviving pigs had relatively normal stools during the entire experiment.

The results are summarized in Table III below.

Table III

Evaluation of the Efficacy of Antibiotic AV290-Tru-Tan RT Regular ® Complex for the Control of Hemorrhagic Colitis in Swine

| Group | Survivors/ Totals | 6 Week Averages of Daily | | Average Body Weight kg./pig | | Average Daily Dosage of AV290 mg./kg. of Body Weight (28 days data) |
|---|---|---|---|---|---|---|
| | | Feed Consumption kg./pig | Weight Gain kg./pig | Start | At 6 Wks. | |
| A Non-infected, Non-medicated | 10/10 | 1.51 | 0.59 | 11.25 | 36.51 | — |
| B Infected, | 0/10 | — | — | 11.20 | — | — |

Table III-continued
Evaluation of the Efficacy of Antibiotic AV290-Tru-Tan RT Regular ® Complex
for the Control of Hemorrhagic Colitis in Swine

| Group | Survivors/ Totals | 6 Week Averages of Daily | | Average Body Weight kg./pig | | Average Daily Dosage of AV290 mg./kg. of Body Weight (28 days data) |
|---|---|---|---|---|---|---|
| | | Feed Consumption kg./pig | Weight Gain kg./pig | Start | At 6 Wks. | |
| Non-medicated C Infected, Medicated, 50 g. AV290 a.i./ton feed | 2/10 | 0.91 | 0.22 | 10.98 | 36.97 | 2.58 |
| D Infected, Medicated 500 g. AV290 a.i./ton feed | 7/10 | 1.43 | 0.47 | 10.75 | 34.38 | 18.07 |

Similar results are obtained by substituting antibiotic AV290, antibiotic AV290 sulfate, another antibiotic AV290-syntan complex, an antibiotic AV290-alkyl sulfate complex, or an AV290 alkylated derivative for antibiotic AV290-Tru-Tan RT Regular ® complex in the above experiment.

EXAMPLE 3

Efficacy of Antibiotic AV290-Lauryl Sulfate Complex for the Control of Hemorrhagic Colitis in Swine By the procedure of Example 2, antibiotic AV290-lauryl sulfate complex (produced by treating antibiotic AV290 with sodium lauryl sulfate) is evaluated incorporated at a rate of 100 ppm in PC-2 swine grower mash with the following results:

Table IV
Effect of Antibiotic AV290-Lauryl Sulfate Complex at 100 ppm in Feed for the Control of Hemorrhagic Colitis

| Drug | Level ppm | Infection | Survivors/ Total | Remarks |
|---|---|---|---|---|
| AV290-lauryl Sulfate | 100 | Yes | 5/10 | One death was not due to swine dysentery |
| Infected Control | 0 | Yes | 1/10 | |
| Non-infected Control | 0 | No | 10/10 | |

I claim:

1. A method of treating hemorrhagic colitis in swine which comprises administering orally to infected swine an effective amount of an antibacterial ingredient selected from the group consisting of antibiotic AV290, antibiotic AV290 sulfate, an antibiotic AV290-syntan complex, an antibiotic AV290-alkyl sulfate complex, an antibiotic AV290 alkylated derivative, and mixtures thereof in any proportion in association with a pharmaceutical carrier to provide a daily dosage of from about 5 mg. to about 50 mg. per kilogram of body weight of said swine.

2. The method according to claim 1 wherein the antibacterial ingredient is antibiotic AV290 sulfate.

3. The method according to claim 1 wherein the antibacterial ingredient is an antibiotic AV290-syntan complex.

4. The method according to claim 1 wherein the antibacterial ingredient is antibiotic AV290-lauryl sulfate complex.

5. The method according to claim 1 wherein the antibacterial ingredient is a 1:1 mixture of antibiotic AV290 and antibiotic AV290 alkylated with ethyl bromide.

* * * * *